United States Patent
Osbrink et al.

(10) Patent No.: US 9,962,528 B2
(45) Date of Patent: May 8, 2018

(54) VARIABLE DIAMETER WOVEN MEDICAL TUBE TEXTILES AND METHOD OF MAKING SAME

(71) Applicant: Cook Medical Technologies LLC, Bloomington, IN (US)

(72) Inventors: Ruth Osbrink, Bloomington, IN (US); David Burton, Bloomington, IN (US); Charlene Phillips, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days. days.

(21) Appl. No.: 15/153,857

(22) Filed: May 13, 2016

(65) Prior Publication Data

US 2017/0021141 A1 Jan. 26, 2017

Related U.S. Application Data

(60) Provisional application No. 62/195,471, filed on Jul. 22, 2015.

(51) Int. Cl.
| | |
|---|---|
| A61F 2/07 | (2013.01) |
| D03D 11/02 | (2006.01) |
| D03D 3/02 | (2006.01) |
| A61M 25/10 | (2013.01) |
| D03D 41/00 | (2006.01) |
| D03D 3/06 | (2006.01) |
| D03D 23/00 | (2006.01) |

(52) U.S. Cl.
CPC ........ *A61M 25/10* (2013.01); *A61M 25/1029* (2013.01); *D03D 3/02* (2013.01); *D03D 3/06* (2013.01); *D03D 41/004* (2013.01); *D10B 2509/06* (2013.01)

(58) Field of Classification Search
CPC ...... A61F 2250/0039; A61F 2250/0017; A61F 2/958; D03D 3/02; D03D 3/06; D03D 41/00; D03D 13/008; D03D 11/02; D03D 3/00; D03D 1/02; D03D 25/005
See application file for complete search history.

(56) References Cited

U.S. PATENT DOCUMENTS

| | | | | |
|---|---|---|---|---|
| 180,790 | A * | 8/1876 | Reed | B05B 1/34 138/123 |
| 444,880 | A * | 1/1891 | Erskine | D03D 3/00 139/387 R |

(Continued)

FOREIGN PATENT DOCUMENTS

| | | |
|---|---|---|
| JP | 2001340366 | 11/2001 |
| JP | 2003275229 | 9/2003 |

(Continued)

*Primary Examiner* — Bobby Muromoto, Jr.
(74) *Attorney, Agent, or Firm* — Liell & McNeil

(57) ABSTRACT

A textile greige includes a plurality of woven medical tube textiles in a series that share a set of warp yarns and a first weft yarn. The medical tube textiles have different diameter segments such that less than all of the warp yarns are included in a small diameter segment of the medical tube textile. A diameter control weave of a second weft yarn is woven with segments of the warp yarns that are outside of the woven medical tube textiles. Later processing includes cutting the diameter control weave from the medical tube textile.

20 Claims, 3 Drawing Sheets

(56) References Cited

U.S. PATENT DOCUMENTS

| | | | |
|---|---|---|---|
| 694,108 A * | 2/1902 | Kaiser | D03D 3/06 |
| | | | 139/190 |
| 2,924,250 A | 2/1960 | Sidebotham | |
| 2,978,787 A * | 4/1961 | Liebig | A61F 2/06 |
| | | | 139/390 |
| 3,016,068 A * | 1/1962 | Felix | D03D 41/00 |
| | | | 139/11 |
| 3,095,017 A * | 6/1963 | Bleiler | A61F 2/06 |
| | | | 139/387 R |
| 3,096,560 A * | 7/1963 | Liebig | A61F 2/06 |
| | | | 139/387 R |
| 3,953,640 A * | 4/1976 | Takada | B60R 21/18 |
| | | | 139/387 R |
| 4,346,741 A * | 8/1982 | Banos | B29C 70/24 |
| | | | 139/387 R |
| 4,668,545 A * | 5/1987 | Lowe | B29C 61/0658 |
| | | | 139/387 R |
| 4,923,724 A * | 5/1990 | Day | B29C 70/222 |
| | | | 139/387 R |
| 5,800,514 A * | 9/1998 | Nunez | A61F 2/06 |
| | | | 139/384 R |
| 5,904,714 A * | 5/1999 | Nunez | A61F 2/06 |
| | | | 139/383 R |
| 6,112,775 A * | 9/2000 | Hossli | D03D 35/00 |
| | | | 139/22 |
| 6,136,022 A * | 10/2000 | Nunez | A61F 2/06 |
| | | | 623/1.1 |
| 6,575,201 B2 | 6/2003 | Buesgen | |
| 6,821,294 B2 * | 11/2004 | Nunez | A61F 2/06 |
| | | | 623/1.3 |
| 6,994,724 B2 * | 2/2006 | Schmitt | A61F 2/04 |
| | | | 139/387 R |
| 7,484,539 B1 * | 2/2009 | Huang | D03D 3/02 |
| | | | 139/384 R |
| 7,550,006 B2 * | 6/2009 | Nunez | A61F 2/06 |
| | | | 623/1.51 |
| 7,758,633 B2 * | 7/2010 | Nazzaro | A61F 2/06 |
| | | | 139/387 R |
| 8,002,741 B2 | 8/2011 | Hayes et al. | |
| 8,696,741 B2 | 4/2014 | Du | |
| 8,834,552 B2 | 9/2014 | Kuppurathanam et al. | |
| 2002/0161388 A1 | 10/2002 | Samuels et al. | |
| 2003/0078650 A1* | 4/2003 | Nunez | A61F 2/06 |
| | | | 623/1.51 |
| 2011/0046654 A1 | 2/2011 | Kuppurathanam | |
| 2012/0171917 A1 | 7/2012 | Rasmussen et al. | |
| 2013/0012967 A1 | 1/2013 | Tani et al. | |
| 2013/0251973 A1 | 9/2013 | Crawford et al. | |
| 2015/0290007 A1* | 10/2015 | Aggerholm | A61F 2/958 |
| | | | 623/1.11 |

FOREIGN PATENT DOCUMENTS

| | | |
|---|---|---|
| WO | 9743983 | 11/1997 |
| WO | 02068011 | 9/2002 |
| WO | 2006034396 | 3/2006 |

* cited by examiner

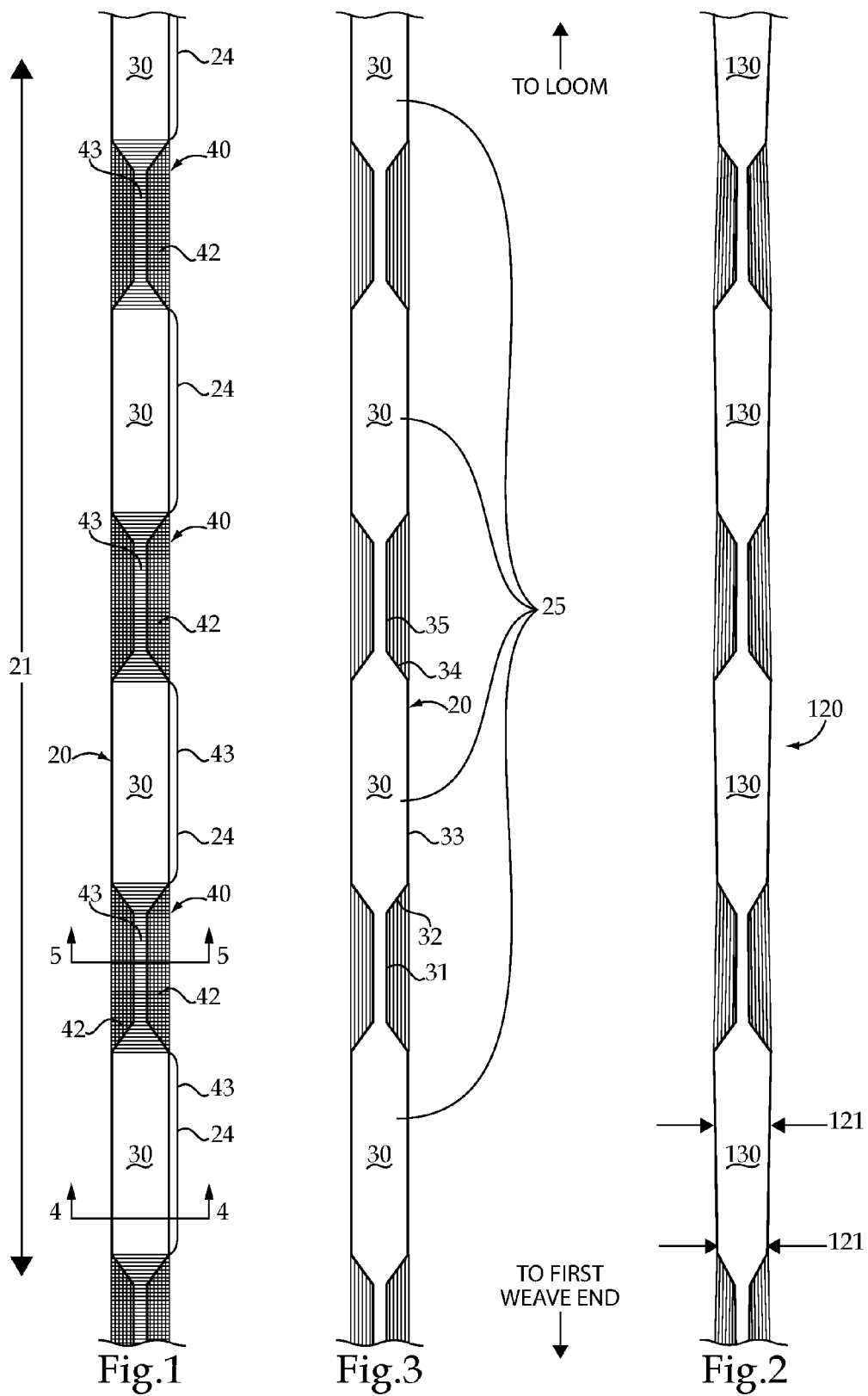

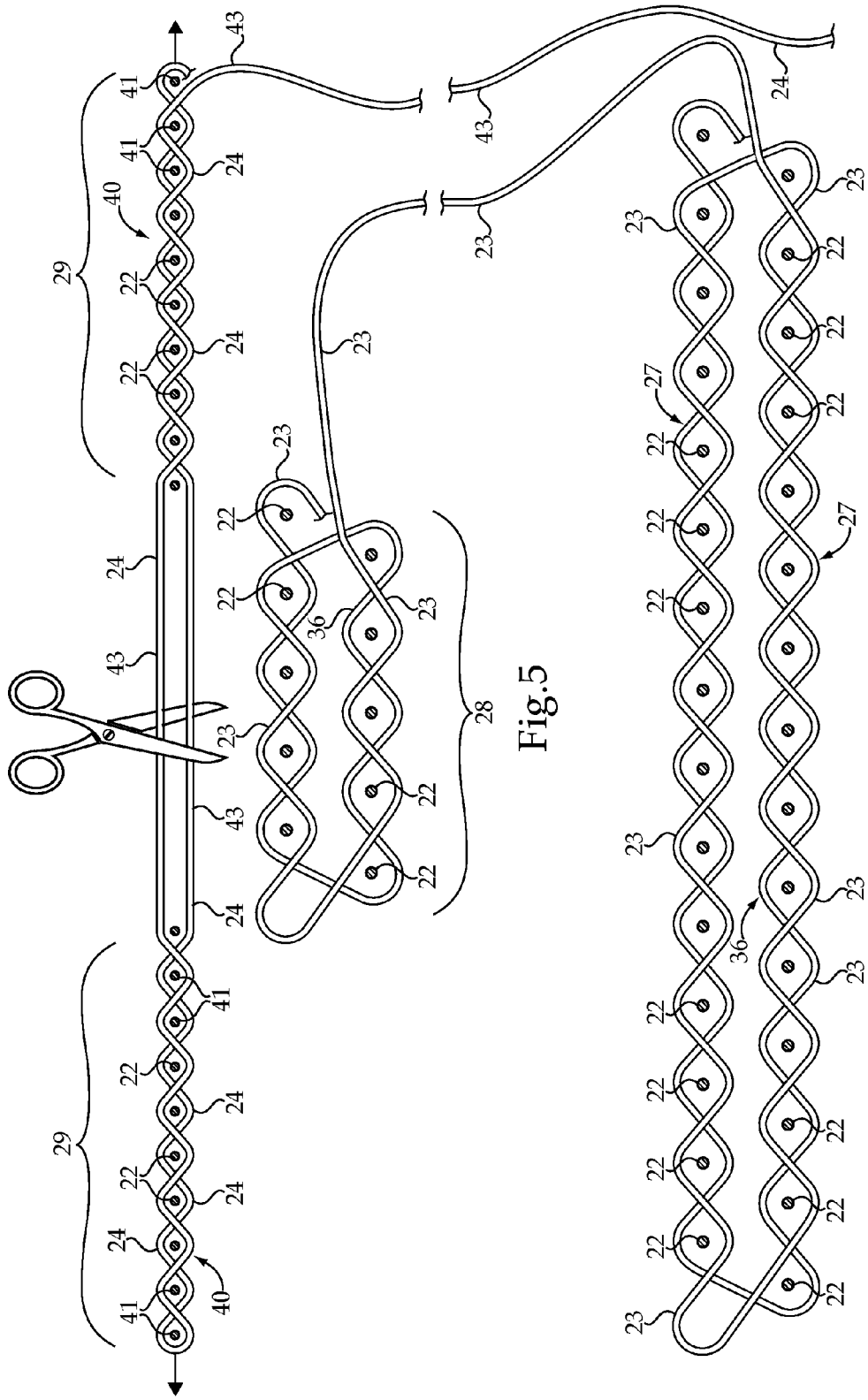

US 9,962,528 B2

VARIABLE DIAMETER WOVEN MEDICAL TUBE TEXTILES AND METHOD OF MAKING SAME

TECHNICAL FIELD

The present disclosure relates generally to woven medical tube textiles having variable diameters along its length, and more particularly to controlling the diameters with a separate diameter control weave.

BACKGROUND

Woven medical tube textiles have been known for many decades. For instance, U.S. Pat. No. 2,924,250 teaches a bifurcated textile tube that is used in the replacement of certain diseased or damaged blood vessels. U.S. Pat. Nos. 5,904,714 and 8,696,741 are of interest for teaching continuously flat-woven implantable tubular prosthesis that have differing diameters along a length of each woven tube. The woven medical tube textiles may start out as parts of a textile greige with a plurality of medical tube textiles woven continuously end to end. Later processing separates the individual medical tube textiles from the textile greige. Although not apparently recognized in the art, controlling the diameter of the medical tube textiles during the weaving process can be problematic in meeting tight tolerances associated with the finished medical tube textile.

The present disclosure is directed toward controlling medical tube textile diameters during the weaving process.

SUMMARY

A textile greige includes a plurality of woven medical tube textiles in a series that share a set of warp yarns and a first weft yarn. A diameter control weave includes a second weft yarn woven with segments of the warp yarns that are outside of the woven medical tube textiles.

In another aspect, a method of making a medical tube textile includes weaving a first weft yarn with a set of warp yarns into a medical tube textile that has a plurality of different diameters along a length. The different diameters are controlled with a diameter control weave by weaving a second weft yarn with segments of the warp yarns that are outside of the medical tube textile.

BRIEF DESCRIPTION OF THE DRAWINGS

FIG. 1 is a front view of a textile greige according to the present disclosure;

FIG. 2 is a front view of a textile greige made without a diameter control weave according to the present disclosure;

FIG. 3 is a front view of the textile greige of FIG. 1 after cutting away the diameter control weave;

FIG. 4 is a sectioned view of the textile greige of FIG. 1 as viewed along section lines 4-4;

FIG. 5 is a sectioned view through the textile greige of FIG. 1 as viewed along section lines 5-5;

DETAILED DESCRIPTION

Figures 6, 7:
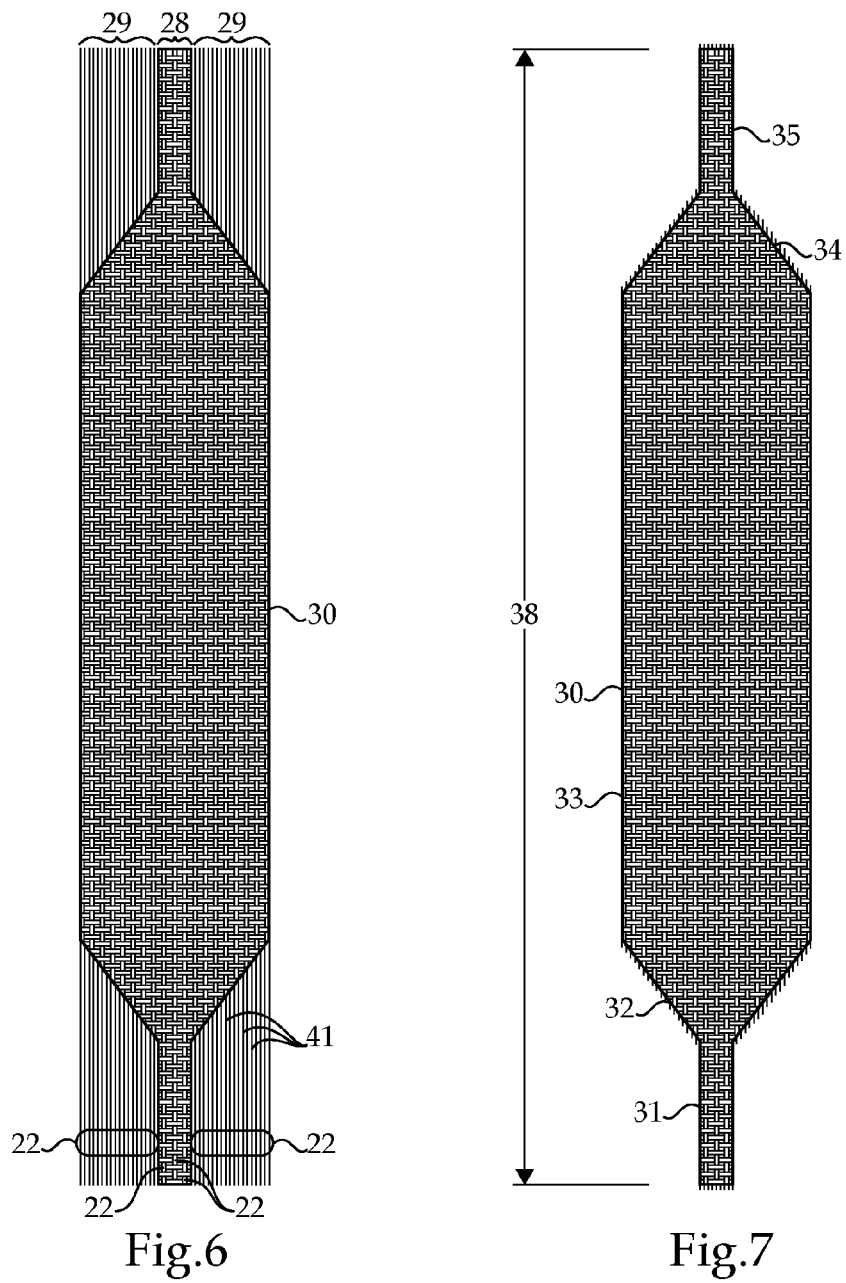
FIG. 6 is a front view of a single woven medical tube textile after removal of the diameter control weave but before the excess warp yarns have been trimmed away.
FIG. 7 is a front view of a medical tube textile according to the present disclosure.

For some applications of medical woven tube textiles, it is critical to maintain tight tolerances on the final dimensions of the woven part. Given a textile part with non-variable geometry, such as a tube with a fixed diameter, such tolerances are achievable with standard weaving techniques. However, for a textile part with variable diameter, typical dimensional tolerances can result in an unacceptably high scrap rate with current weaving techniques. This dimensional difficulty is sometimes demonstrated in the set-up to weave a textile of a fixed diameter. After the yarns have been threaded through the loom, a set length of material will be woven and scrapped before the textile part dimensions are considered to have stabilized. Multiple known and maybe some unknown factors contribute to the irregular dimensions of parts with variable diameters. Among these are weft shuttle tension, warp yarn tension, the amount of contact between warp yarn and the take up rollers of the loom, and the extent to which warp yarns have already been incorporated into the weave. These factors are largely mitigated if the woven part has non-variable geometry.

One specific example that illustrated dimensional problems is shown in FIG. 2. FIG. 2 shows a textile greige 120 in which a plurality of woven medical tube textiles 130 are in a series that share a set of warp yarns and a weft yarn. As used in this disclosure, "greige" means an unfinished weave, which are unfinished at least because individual medical tube textiles 130 have not yet been cut from the weave. Textile greige 120 shows four woven medical tube textiles 130 shaped for use as a portion of the high pressure balloon catheter. Medical tube textiles 130 are shown white in order to emphasize the variable width of the overall weave, and show warp yarn segments that are left unwoven. Each of the medical tube textiles 130 should have a relatively elongate segment with a uniform diameter in the finished product, which relates to the width 121 of textile greige 120. The medical tube textiles 130 are woven in the flat using well known techniques and weaving strategies that need not be taught again here. Toward the bottom of FIG. 2, the drawings show that the initial portion of the width 121 is smaller than the width 121 toward the opposite end of the medical tube textile due to the conventional tolerance issues identified above. Because the dimensional width problem is apparently initialized between each of the medical tube textiles 130, every one of the medical tube textiles 130 suffers from a similar, and unacceptable width variation, leaving all of the medical tube textiles 130 unusable as scrap.

The present disclosure addresses this conventional tolerancing issue in a fashion that makes it appear, at least in the textile greige stage of manufacture, to have a non-variable geometry. This may be achieved with the use of a second weft yarn that is woven with warp yarn segments that are outside of the medical tube textile 30. Thus, the first weft yarn is utilized for making the desired medical tube textile 30, similar to the manner shown in FIG. 2, and a second weft yarn serves as a stabilizer being woven everywhere that the first weft yarn is not. Together, the two weft system gives the textile greige 20 the appearance, and the dimensional stability of a tube with non-variable geometry. Following weaving, the second weft yarn may be cut and removed, resulting in a variable geometry part that can hold tight dimensional tolerances.

Referring now to FIGS. 1, 4 and 5, a textile greige 20 includes a plurality of woven medical tube textiles 30 in a series 21 that share a set of warp yarns 22 and a first weft yarn 23. A diameter control weave 40 includes a second weft yarn 24 woven with segments 41 of the warp yarns 22 that are outside of the woven medical tube textiles 30. In the illustrated embodiment, the plurality of medical tube textiles 30 are segments of a continuous weave 25 along the warp yarns 22. However, some discontinuity between successive medical tube textiles 30 could also fall within the intended scope of the present disclosure. Medical tube textiles 30 are shown as white to emphasize how the textile greige 20 of FIG. 1 differs from that of FIG. 2. In the illustrated embodiment, the diameter control weave 40 includes a plurality of discontinuous woven areas 42 connected by unwoven segments 43 of the second weft yarn 24. The diameter control weave 40 may be contiguous with the medical tube textiles 30. Nevertheless, acceptable dimensional stability may still be maintained if some unwoven space is left between the medical tube textiles 30 and the diameter control weave 40, and still fall within the intended scope of the present disclosure. Also, the diameter control weave 40 could be partially woven into the medical tube textiles 30 (and later cut away) without departing from the present disclosure. In the illustrated embodiment, and as shown in FIG. 3 each of the medical tube textiles 30 may include a large diameter segment 33 and a small diameter segment 35. Less than all of the warp yarns 22 are included in the weave that defines the small diameter segment 35. Although not necessary, the medical tube textiles 30 in the present disclosure have at least one uniform diameter segment 33 that is contiguous with at least one tapered diameter segment 32, as shown in FIG. 3. Nevertheless, those skilled in the art will appreciate that a wide variety of variable geometry medical tube textiles without these features could also fall within the intended scope of the present disclosure. In the illustrated embodiment, the warp yarns 22 and the first weft yarn 23 may be suitable medical grade man made monofilament fibers, but one or both could be multi-filament fibers without departing from the intended scope of this disclosure. Furthermore, in one specific application, the warp yarns 22 and the first weft yarn 23 are identical man made monofilaments. The second weft yarn 24 may be identical to one or both of the warp yarns 22 and the first weft yarn 23, or may be multi-filament, or natural fibers, or sized different from the warp yarns 22 and first weft yarn 23 without departing from the present disclosure.

As best shown in FIG. 4, a wall 36 of each medical tube textile 30 may have a plain weave pattern 27. However, other weave patterns for the wall 36 of each of the medical tube textiles 30 could be different from a plain weave pattern 27 without departing from the present disclosure. For instance, medical tube textile 30 could have a twill or diamond weave pattern without departing from the present disclosure. The woven medical tube textiles 30 and the diameter control weave 40 may have independent weave patterns, as best shown in FIG. 5. In particular, in FIG. 5, in the illustrated embodiment, the warp yarns for the small diameter segment 35 have a tubular weave pattern that yields tube walls 36 that have a plain weave pattern 27. The diameter control weave 40 is shown to have a simple plain weave pattern. Nevertheless, the diameter control weave 40 could also have a tube weave pattern that is identical to the weave pattern utilized to generate the medical tube textiles 30. Of importance, is a weave pattern for the diameter control weave 40 that is sufficient to maintain dimensional stability in the woven medical tube textiles 30. Thus, one skilled in the art might choose an independent weave pattern for the diameter control weave 40 that is sufficient to maintain stability in the woven medical tube textiles 30, but the weave pattern is chosen to not significantly slow the overall weaving process for textile greige 20. Other considerations, such as ease of detaching the diameter control weave from the medical tube textile 30, might also contribute to deciding on a weave pattern for the diameter control weave 40.

Figure 8:
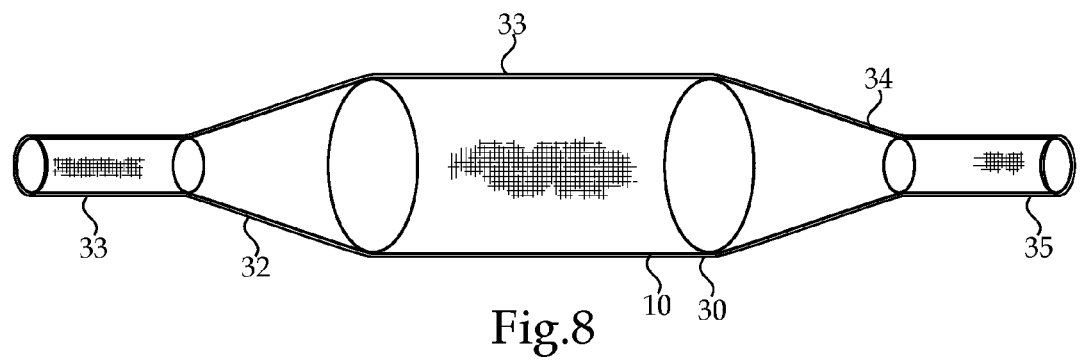
FIG. 8 is a perspective view of an inflated medical balloon with a medical tube textile according to the present disclosure.

Referring in addition to FIGS. 6 and 7, after weaving the textile greige 20 of FIG. 1, individual medical tube textiles 30 may be cut from textile greige 20 before or after the diameter controlled weave 40 has been cut and removed. FIG. 3 shows the textile greige 20 of FIG. 1 after the diameter control weave 40 has been cut and removed. In particular, FIG. 3 shows textile greige 20 after removal of the second weft yarn 24. FIG. 6 shows a segment of textile greige 20 that includes a single medical tube textile 30 with segments 41 of the warp yarns 22 that were included in the diameter control weave 40. These excess warp yarn segments 41 may be cut away to yield a single medical tube textile 30, as shown in FIG. 7 that includes a first small diameter segment 31, a first tapered segment 32, a large diameter segment 33, a second tapered segment 34 and a second small diameter segment 35. In the illustrated embodiment, the medical tube textile 30 is shaped to match an inflated medical balloon 10, as shown in FIG. 8.

INDUSTRIAL APPLICABILITY

The present disclosure finds general applicability to woven tubular textiles that have a variable geometry along a length of the textile. The present disclosure finds specific applicability to woven medical tube textiles that have a variable geometry along its length, such as woven medical tube textiles utilized with high pressure balloon catheters.

Medical tube textiles 30 according to the present disclosure may be made by weaving a first weft yarn 23 with a set of warp yarns 22 into a medical tube textile 30 having a plurality of different diameters along a length 38. The different diameters that make up the medical tube textile 30 are controlled with a diameter control weave 40. The diameter control weave 40 is created by weaving a second weft yarn 24 with segments 41 of the warp yarns 22 that are outside of the medical tube textile 30. Although not necessary, the process may include weaving a plurality of medical tube textiles 30 in a series 21 using the first weft yarn 23 and the warp yarns 22 in a series to form a textile greige 20 as shown in FIG. 1. Although not necessary, in the illustrated embodiment, the second weft yarn 24 is woven with less than all of the warp yarns 29. Thus, the segments of the warp yarns 22 that make up the small diameter segments 31 and 35 may include no segments that are woven with the second weft yarn 24. Nevertheless, if there was some discontinuity between successive medical tube textiles 30, it is possible that the second weft yarn 24 could be woven with all of the warp yarns 22 at different locations without departing from the present disclosure. Thus, in the illustrated embodiment, the textile greige 20 includes a plurality of medical tube textiles 30 that are segments of a continuous weave 25 along the warp yarns 22. As stated earlier, in the illustrated embodiment, the diameter control weave 40 includes a plurality of discontinuous woven areas 42 connected by an unwoven segment 43 of the second warp yarn 24. In the illustrated embodiment, the first weft yarn 23 is woven with the warp yarns 22 to yield a plain weave pattern 27 in a wall 36 of the medical tube textile 30. Nevertheless, those skilled in the art will appreciate that the walls 36 of the medical tube textile 30 could be woven to include something other than a plain weave pattern without departing from the intended scope of the present disclosure. It should be noted that the first weft yarn 23 is oriented substantially perpendicular to the weft yarns 22 in the medical tube textile 30. Nevertheless, something other than a perpendicular weaving arrangement might still fall within the intended scope of the present disclosure. In the illustrated embodiment, less than all of the warp yarns 29 may be woven with the second weft yarn 24, and a different subset of less than all the warp yarns 28 are included in the small diameter segments 31, 35, as best shown in FIG. 5.

When the second weft yarn 24 is cut away from the medical tube textile 30 may be a matter of choice. In the illustrated embodiment, FIG. 3 shows the second weft yarn 24 as having been cut away and removed from the textile greige 20 before the individual medical tube textiles 30 have been cut from the textile greige 20 to length, as shown in FIG. 6. Nevertheless, the second weft yarn 24 may be cut from the medical tube textile 30 after the textile greige 20 has had individual medical tube textiles 30 cut therefrom to length. After the excess warp yarn segments 41 are cut away from the medical tube textile 30 as shown in FIG. 7, later processing may be utilized to match and attach the medical tube textiles 30 to individual medical balloons 10 as schematically shown in FIG. 8.

The method of the present disclosure may be applied to the weaving of any textile tube part with variable geometry where dimensional tolerances need to be held. A weaving program could be created in a weave design software such as EATS Design Scope Victor to specify the use of two weft yarn systems and identify where each weft yarn system would be incorporated as described previously. The loom, which could be a computer controlled Jacquard loom, could be set up with two weft yarn shuttles to correspond with the weave design program part. As discussed earlier, the individual textile tube parts would be woven and then undergo post-weave processing to remove the second weft yarn 24. In the illustrated embodiment, the weave design program, the weft density (number of weft yarns per inch) might be doubled to accommodate the second weft yarn 24. The two weft yarns 23, 24 could alternate between two passes of the first weft yarn shuttle (not shown) and two passes of the second weft yarn shuttle (not shown) if the weave patterns are both for yielding tube weaves. Alternatively, as illustrated in the embodiment shown in FIG. 5, the weft yarns could alternate between two passes of the first weft yarn 23, and a single pass of the second weft yarn 22, if the diameter control weave has a plain weave pattern. Those skilled in the art will recognize that the tubular segments 31, 32, 33, 34 and 35 require four passes of the first weft yarn 23 to complete each segment of the weave, as shown in FIGS. 4 and 5.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. A textile greige comprising:
   a plurality of the woven medical tube textiles in a series that share a set of warp yarns and a first weft yarn;
   a diameter control weave of a second weft yarn with segments of at least a portion of the warp yarns that are outside of the woven medical tube textiles such that the diameter control weave is not part of, and is separable from, the plurality of woven medical tube textiles.

2. The textile greige of claim 1 wherein the first weft yarn is a monofilament; and
   each of the warp yarns is a monofilament.

3. The textile greige of claim 1 wherein each of the medical tube textiles has at least one uniform diameter segment contiguous with at least one tapered diameter segment.

4. The textile greige of claim 1 wherein the diameter control weave is contiguous with the medical tube textiles.

5. The textile greige of claim 1 wherein each of the medical tube textiles includes a large diameter segment and a small diameter segment; and
   less than all of warp yarns are included in the small diameter segment.

6. The textile greige of claim 1 wherein the woven medical tube textiles and the diameter control weave have independent weave patterns.

7. The textile greige of claim 1 wherein the plurality of medical tube textiles are segments of a continuous weave along the warp yarns; and
   the diameter control weave includes a plurality of discontinuous woven areas connected by unwoven segments of the second weft yarn.

8. The textile greige of claim 1 wherein each of the medical tube textiles includes a first small diameter segment, a first tapered diameter segment, a large diameter segment, a second tapered diameter segment and a second small diameter segment.

9. The textile greige of claim 8 wherein each of the first weft yarn and the warp yarns is a monofilament.

10. The textile greige of claim 9 wherein each of the medical tube textiles is shaped to match an inflated medical balloon.

11. The textile greige of claim 10 wherein a wall of each of the medical tube textiles has a plain weave pattern.

12. A method of making a medical tube textile comprising the steps of:
    weaving a first weft yarn with a set of warp yarns into a medical tube textile having a plurality of different diameters along a length;
    controlling the different diameters with a diameter control weave by weaving a second weft yarn with segments of at least a portion of the warp yarns that are outside of the medical tube textile such that the diameter control weave is not part of, and is separable from, the plurality of woven medical tube textiles.

13. The method of claim 12 wherein the step of weaving the first weft yarn includes weaving a plurality of the medical tube textiles in a series using the set of warp yarns into a textile greige.

14. The method of claim 13 wherein the second weft yarn is woven with less than all the warp yarns.

15. The method of claim 13 wherein the textile greige includes the plurality of medical tube textiles as segments of a continuous weave along the warp yarns; and
    the diameter control weave includes a plurality of discontinuous woven areas connected by unwoven segments of the second weft yarn.

16. The method of claim 12 wherein the step of weaving the first weft yarn is performed to yield a plain weave pattern in a wall of the medical tube textile.

17. The method of claim 12 wherein the medical tube textile and the diameter control weave have independent weave patterns.

18. The method of claim 12 wherein the first weft yarn is oriented perpendicular to the warp yarns in the medical tube textile.

19. The method of claim 12 wherein the medical tube textile includes a large diameter segment and a small diameter segment; and
    less than all of the warp yarns are included in the small diameter segment.

20. The method of claim 12 including cutting the diameter control weave from the medical tube textile.

* * * * *